United States Patent
Ferek-Petric (10) Patent No.: US 7,317,943 B2
(45) Date of Patent: Jan. 8, 2008

(54) CAPTURE THRESHOLD MONITORING

(75) Inventor: Bozidar Ferek-Petric, Zagreb (HR)

(73) Assignee: Medtronic, Inc., Minneapolis, MN (US)

( * ) Notice: Subject to any disclaimer, the term of this patent is extended or adjusted under 35 U.S.C. 154(b) by 509 days.

(21) Appl. No.: 10/356,259

(22) Filed: Jan. 31, 2003

(65) Prior Publication Data

US 2004/0172082 A1    Sep. 2, 2004

(51) Int. Cl.
*A61N 1/08* (2006.01)

(52) U.S. Cl. .............. 607/28; 607/7; 607/8; 607/27; 607/32

(58) Field of Classification Search .............. 607/7–8, 607/27–28, 32
See application file for complete search history.

(56) References Cited

U.S. PATENT DOCUMENTS

| | | | |
|---|---|---|---|
| 4,574,810 A * | 3/1986 | Lerman | 607/8 |
| 4,729,376 A * | 3/1988 | DeCote, Jr. | 607/28 |
| 5,330,513 A | 7/1994 | Nichols et al. | |
| 5,447,525 A * | 9/1995 | Powell et al. | 607/28 |
| 5,480,414 A * | 1/1996 | Stroebel et al. | 607/28 |
| 5,792,202 A | 8/1998 | Rueter | |
| 6,129,746 A | 10/2000 | Levine et al. | |
| 6,249,702 B1 | 6/2001 | Van Oort | |
| 6,456,881 B1 | 9/2002 | Bornzin et al. | |
| 6,587,723 B1 * | 7/2003 | Sloman et al. | 607/28 |
| 6,697,673 B1 * | 2/2004 | Lu | 607/28 |
| 6,731,985 B2 * | 5/2004 | Poore et al. | 607/28 |
| 6,738,668 B1 * | 5/2004 | Mouchawar et al. | 607/28 |
| 6,766,197 B1 * | 7/2004 | Levine | 607/27 |
| 6,915,164 B2 * | 7/2005 | Bradley et al. | 607/29 |
| 6,928,325 B2 * | 8/2005 | Zhu et al. | 607/28 |

OTHER PUBLICATIONS

Brochure, Medtronic, Inc., "Kappa 700: Follow-up with TMT and Fast Telemetry," 6 pgs. (1998).

* cited by examiner

*Primary Examiner*—Carl Layno
*Assistant Examiner*—Deborah Malamud
(74) *Attorney, Agent, or Firm*—Daniel G. Chapik (57) ABSTRACT

In general, the invention is directed to techniques for capture testing of a capture threshold in cooperation with measurement of other cardiac parameters. Physiological or non-physiological parameters may indicate a possible change in the capture threshold, and a significant change in a cardiac parameter may trigger more frequent monitoring of the capture threshold. In addition, measurement of cardiac parameters in relation to measurement of the capture threshold may be useful in diagnosing problems and forecasting possible loss of capture.

8 Claims, 4 Drawing Sheets

CAPTURE THRESHOLD MONITORING

TECHNICAL FIELD

The invention relates to implantable devices having an implantable pulse generator (IPG) for cardiac stimulation, and more particularly, to capture management by these devices.

BACKGROUND

An implantable medical device such as a cardiac pacemaker supplants some or all of the natural pacing function of a heart by delivering appropriately timed electrical stimulation signals designed to cause the myocardium of the heart to contract. An implantable pulse generator (IPG) in the device generates the electrical stimuli. To be effective, the stimuli should be of a sufficient strength (or amplitude) and duration (or pulse width) to cause the heart to beat, i.e., to "capture" the heart. A "capture threshold" or "stimulation threshold" defined by a strength-duration curve separates stimuli that capture the heart from stimuli that fail to capture the heart.

Because a failure to capture the heart may result in serious complications or death, pacing stimuli are generally delivered with a strength and duration above the capture threshold by a safety margin. It is generally desirable, however, that the safety margin be reasonably large enough to ensure capture but small enough that power not be wasted. Implantable medical devices that draw power from a battery have a limited power supply, and the strength and duration of the stimuli should be regulated to prolong battery life. The strength and duration of stimuli may be set or adjusted with programming equipment that communicates with the implantable medical device.

Over time, the capture threshold can change. The change in capture threshold may be due to physiological factors, such as the physical condition of a patient or drug concentrations in the body of the patient. The threshold may also change due to non-physiological factors. For example, a lead that delivers stimuli to the myocardium may lose insulation or a filament in a lead having multifilar construction may break.

Because the capture threshold may change over time, a stimulation that may capture the heart at one point in time may fail to capture the heart at a later point in time. Accordingly, many implantable medical devices include the capability of automatically testing and measuring the capture threshold, in a process called "capture testing." The devices may automatically adjust the strength or duration of the pacing stimuli as a result of the outcome of the capture testing. Conventional implantable medical devices measure the capture threshold on a substantially periodic basis, such as one time per day while the patient is at rest. The frequency of testing the threshold to assure capture is called the "capture test frequency."

SUMMARY

In general, the invention presents techniques for cardiac capture testing in cooperation with measurement of other cardiac parameters. Changes in other cardiac parameters may be indicative of a possible change in the capture threshold, and in some circumstances it may be beneficial to monitor the capture threshold more closely by measuring the capture threshold more frequently. Accordingly, a significant change in a cardiac parameter such as lead impedance may trigger an increase in the capture test frequency.

In one embodiment, the invention is directed to a method comprising automatically performing a cardiac capture test at a first capture test frequency, detecting a substantial change in at least one cardiac parameter and automatically performing the capture test at a second capture test frequency greater than the first capture test frequency, in response to the detection of the substantial change.

A "cardiac parameter" may pertain to physiological or non-physiological factors, such as the performance of an implantable medical device or a physiologic condition of a patient. Examples of cardiac parameters include an impedance of a lead used to deliver cardiac stimuli to a patient, a change in a blood pressure of the patient, a change in a cardiac waveform of the patient, a change in cardiac hemodynamics of the patient and a change in heart contractility of the patient.

In addition, other cardiac parameters may be useful in identifying problems and forecasting possible loss of capture. When data are recorded that relate substantially contemporaneous measurements of the capture threshold and a cardiac parameter, the data may indicate a trend. For example, increases in lead impedance accompanied by increases in the capture threshold may indicate a problem with an implanted lead.

In another embodiment, therefore, the invention is directed to a method comprising performing a capture test to measure a capture threshold, measuring a cardiac parameter substantially contemporaneously with the performance of the capture test and recording data representing the capture threshold in relation to the measurement of the cardiac parameter. The method may also include performing a trend analysis as a function of the recorded data, and generating an alert as a function of the trend analysis.

The invention further includes computer-readable media comprising instructions for causing a programmable processor to carry out the methods described above.

In a further embodiment, the invention is directed to a device comprising a sensor to detect a cardiac parameter comprising one of a performance of an implantable medical device and a physiologic condition of a patient other than a capture threshold. The device also includes a processor to automatically perform a capture test at a first capture test frequency and to automatically perform the capture test at a second capture test frequency greater than the first capture test frequency upon detection of a substantial change in the cardiac parameter. The processor may further be configured to measure a capture threshold with the capture test, to measure the detected cardiac parameter and to record data representing the capture threshold in relation to the measurement of the cardiac parameter.

The invention may have one or more advantages. Conventional capture tests are typically performed infrequently, because they substantially tax the power supply of an implantable medical device. The invention presents techniques for increasing the frequency of capture tests when physiological or non-physiological factors indicate that the capture threshold should be monitored more closely. In this manner, an implantable medical device increases capture test frequency on a selective basis in response to sensed events. By applying these techniques, an implantable medical device may receive early warning of potential problems with the capture threshold.

In addition, relating the capture threshold to another cardiac parameter may be advantageous. The relationship may be useful to understand what is occurring, and to predict potential problems with loss of capture. In some cases, an implantable medical device may issue an alert when a trend analysis indicates that a loss of capture may occur.

The details of one or more embodiments and aspects of the invention are set forth in the accompanying drawings and the description below. aspects and features of the invention will be apparent from the description and drawings, and from the claims.

DETAILED DESCRIPTION

Figure 1:
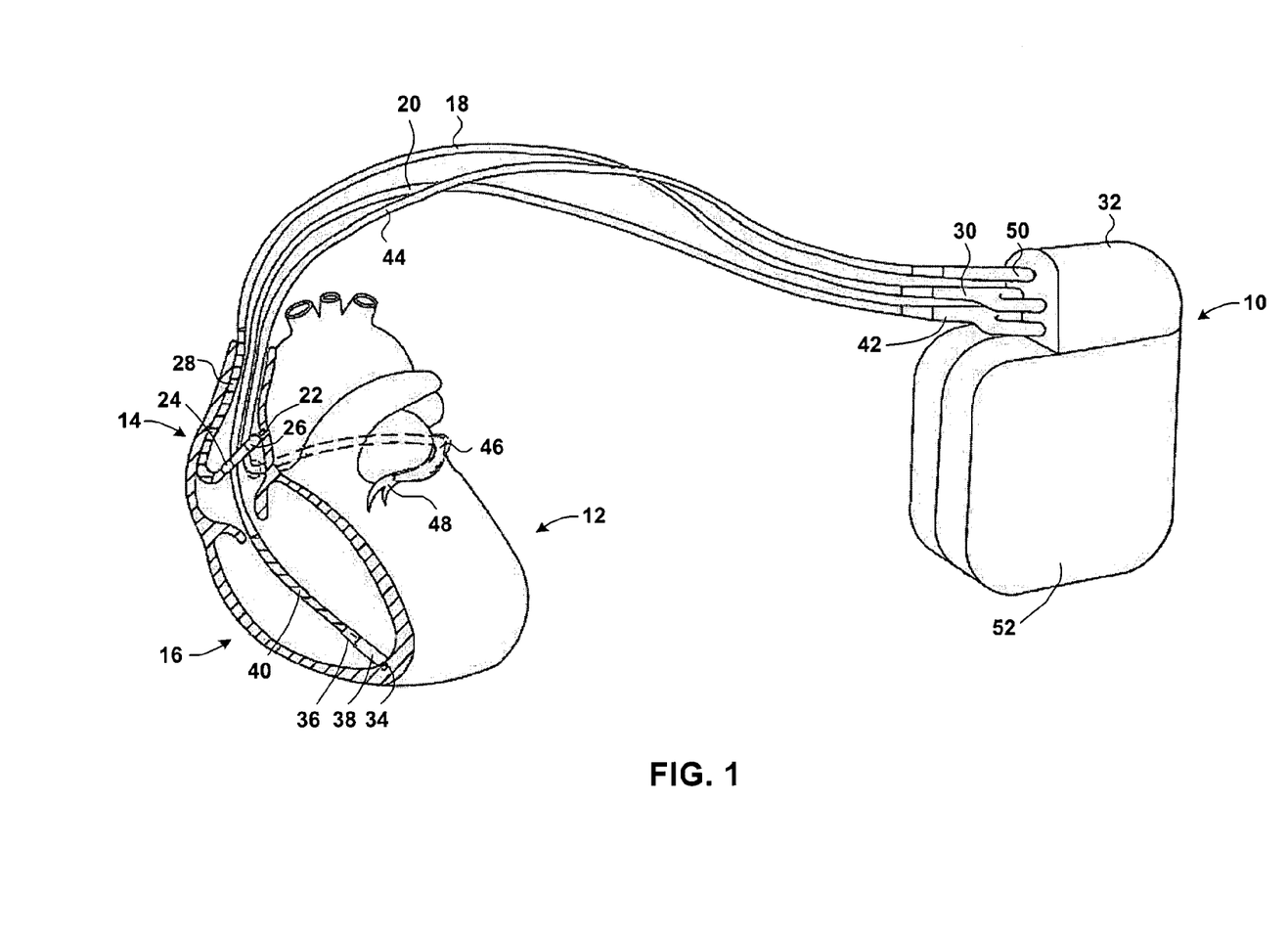
FIG. 1 is a schematic illustration of an atrial and ventricular chamber pacemaker/cardioverter/defibrillator with leads extending to a human heart.

FIG. 1 depicts an exemplary implantable medical device (IMD) 10 that may practice the techniques of the invention. IMD 10 is an implantable multi-chamber pacemaker that includes cardioversion and defibrillation capability. The invention is not limited to the particular IMD shown in FIG. 1, however, but may be practiced by any number of implantable devices. The techniques of the invention may be practiced by a device that paces a single cardiac chamber or several chambers, that paces one or more atria or one or more ventricles, that includes or lacks cardioversion and defibrillation capability, and that paces in any pacing mode.

IMD 10 includes an implantable pulse generator (IPG) (not shown in FIG. 1) that generates pacing stimuli or pulses to activate and cause depolarization of regions of the heart 12. In the embodiment shown in FIG. 1, pacing stimuli or pulses may be applied to the right atrium 14 or the right ventricle 16, or both, depending upon the pacing mode. IMD 10 also includes circuitry to sense atrial and ventricular activations. Atrial and ventricular bipolar pace/sense electrode pairs at the distal ends of leads 18 and 20, respectively, carry out the pacing and sensing functions.

In right atrium 14, the distal end of atrial lead 18 includes an extendable helical, pace/sense tip electrode 22 and a pace/sense ring electrode 24. Helical electrode 22 extends from electrode head 26 into the atrial appendage. Pace/sense electrodes 22 and 24 are employed for atrial pacing and for sensing of P-waves indicative of atrial activation. The distal end of atrial lead 18 also includes an elongated coil defibrillation electrode 28 that can deliver a defibrillation shock to right atrium 14.

Atrial lead 18 may include conductors that electrically couple electrodes 22, 24 and 28 to IMD 10. The conductors may be arranged coaxially, coradially, in parallel, or in another configuration, and may be insulated from one another and from the tissue of the patient. The conductors may be multifilar conductors, i.e., the conductors may include a plurality of conducting filaments. The proximal end of atrial lead 18 may include a bifurcated connector 30 that couples the conductors to a connector block 32 on IMD 10.

In right ventricle 16, the distal end of ventricular lead 20 likewise may include a pace/sense tip electrode 34 and a pace/sense ring electrode 36. Pace/sense tip electrode 34 may be a helical electrode that extends from electrode head 38 toward the apex of heart 12. Pace/sense electrodes 34 and 36 are employed for ventricular pacing and for sensing of R-waves indicative of ventricular activation. The distal end of ventricular lead 20 also includes an elongated coil defibrillation electrode 40 that can deliver a defibrillation shock to right ventricle 16.

Like atrial lead 18, ventricular lead 20 may include insulated multifilar conductors that electrically couple electrodes 34, 36 and 40 to IMD 10. The proximal end of ventricular lead 20 may include a bifurcated connector 42 that couples the conductors to connector block 32.

FIG. 1 also illustrates deployment of a coronary sinus lead 44. Coronary sinus lead 44 may include one or more insulated multifilar conductors. The proximal end of coronary sinus lead 44 may include one or more electrodes, such as an elongated exposed coil wire defibrillation electrode 46. Defibrillation electrode 46, illustrated in broken outline, is located within the coronary sinus and great vein 48 of heart 12. A connector 50 at the proximal end of the coronary sinus lead 44 couples the conductors in lead 44 to connector block 32.

IMD 10 includes a housing 52 that, in some embodiments of the invention, serves as a "can" electrode. In unipolar operation, IMD 10 may deliver an electrical stimulation to heart 12 via an electrode disposed on one or more of leads 18, 20 or 44, with housing 52 being a part of the return current path. In bipolar operation, by contrast, IMD 10 may deliver an electrical stimulation to heart 12 via a tip electrode, with a ring electrode providing the principal return current path.

In the embodiment depicted in FIG. 1, IMD 10 delivers pacing stimuli to right atrium 14 and right ventricle 16 via electrodes 22 and 34, respectively, and senses atrial and ventricular activations via the same electrodes. In the event of capture, the pacing stimuli cause the cardiac chambers to activate. In the event capture fails, the pacing stimuli fail to cause the cardiac chambers to activate.

Failure to capture may be caused by a change in the capture threshold. Such a change may be due to physiological factors. The tissue stimulated by the pacing stimuli may lose conductivity over time, for example, resulting in an increase in the capture threshold. Some physiological conditions, such as a concentration of a chemical in the body, may affect the capture threshold temporarily. Changes in the capture threshold because of physiological factors may have undesirable effects. In particular, a stimulation that may capture the heart at one point in time may fail to capture the heart at a later point in time.

A change in the capture threshold may also be caused by non-physiological factors that affect the performance of IMD 10. For example, damage to a lead that delivers the stimuli may affect the ability of IMD 10 to capture the heart. Even though there may be no physiological change to the capture threshold, IMD 10 may nevertheless perceive a change in the capture threshold because of factors affecting the performance of IMD 10. Because of these factors, a stimulation that may capture the heart at one point in time may fail to capture the heart at a later point in time.

Because of possible changes to the capture threshold due to physiological or non-physiological factors, IMD 10 may automatically perform a cardiac capture test to test and measure the capture threshold. IMD 10 may also adjust the strength or duration of the pacing stimuli in response to changes in the threshold.

There are many techniques for performing a capture test, and the invention is not limited to any particular technique. For example, IMD 10 may deliver to heart 12 a series of pacing pulses of varying strengths or durations or both, and may record which pulses capture heart 12 and which pulses do not. In this way, the capture threshold may be determined experimentally.

In addition to capture testing, IMD 10 may measure other cardiac parameters as well. The cardiac parameters may pertain to the performance of heart 12 or to the performance of IMD 10 with leads and electrodes. Some cardiac parameters may pertain both to physiologic and non-physiologic factors. For example, IMD 10 may analyze the timing or morphology or both of cardiac electrical activity sensed via electrodes 22, 24, 34 and 36. Analysis of the electrical activity may be useful in measuring various timing intervals, for example, or in assessing the efficiency of intrinsic cardiac function or responses to cardiac pacing.

IMD 10 may also measure the lead impedance of leads 18 and 20, by relating the quantity of current sent through a lead to the voltage potential needed to send that quantity of current. Lead impedance may change due to physiologic and non-physiologic factors. Growth of fibrous tissue or the development of necrosis near a pacing site are examples of physiologic factors that may cause a change in lead impedance. A loss of insulation or the fracture of a filament in a multifilar lead are examples of non-physiologic factors that may cause a change in lead impedance.

In some embodiments of the invention, atrial lead 18 or ventricular lead 20 or both may include a sensor responsive to a cardiac parameter other than electrical activity. For example, atrial lead 18 or ventricular lead 20 or both may include a pressure sensor responsive to the blood pressure in right atrium 14 or right ventricle 16. Pressure signals from pressure sensors in heart 12 may be conveyed to IMD 10 via lead 18 or lead 20 or both. IMD 10 may analyze the pressure signals to identify blood pressures that may be of clinical significance, such as right ventricular peak systolic pressure or estimated pulmonary artery diastolic pressure.

As will be described in more detail below, measurement of cardiac parameters such as lead impedance, heart contractility or hemodynamics, cardiac intervals and chamber pressures may be related to the capture threshold. A change in lead impedance, for example, may indicate that a stimulus that has successfully captured the heart in the past possibly may fail to capture the heart in the future. In accordance with one or more embodiments of the invention, IMD 10 may change the capture test frequency in response to changes in these cardiac parameters. In particular, IMD 10 may perform a capture test to measure the capture threshold more frequently than normal. IMD 10 may also relate the measured capture threshold to one or more cardiac parameters, and may evaluate the data for trends.

Figure 2:
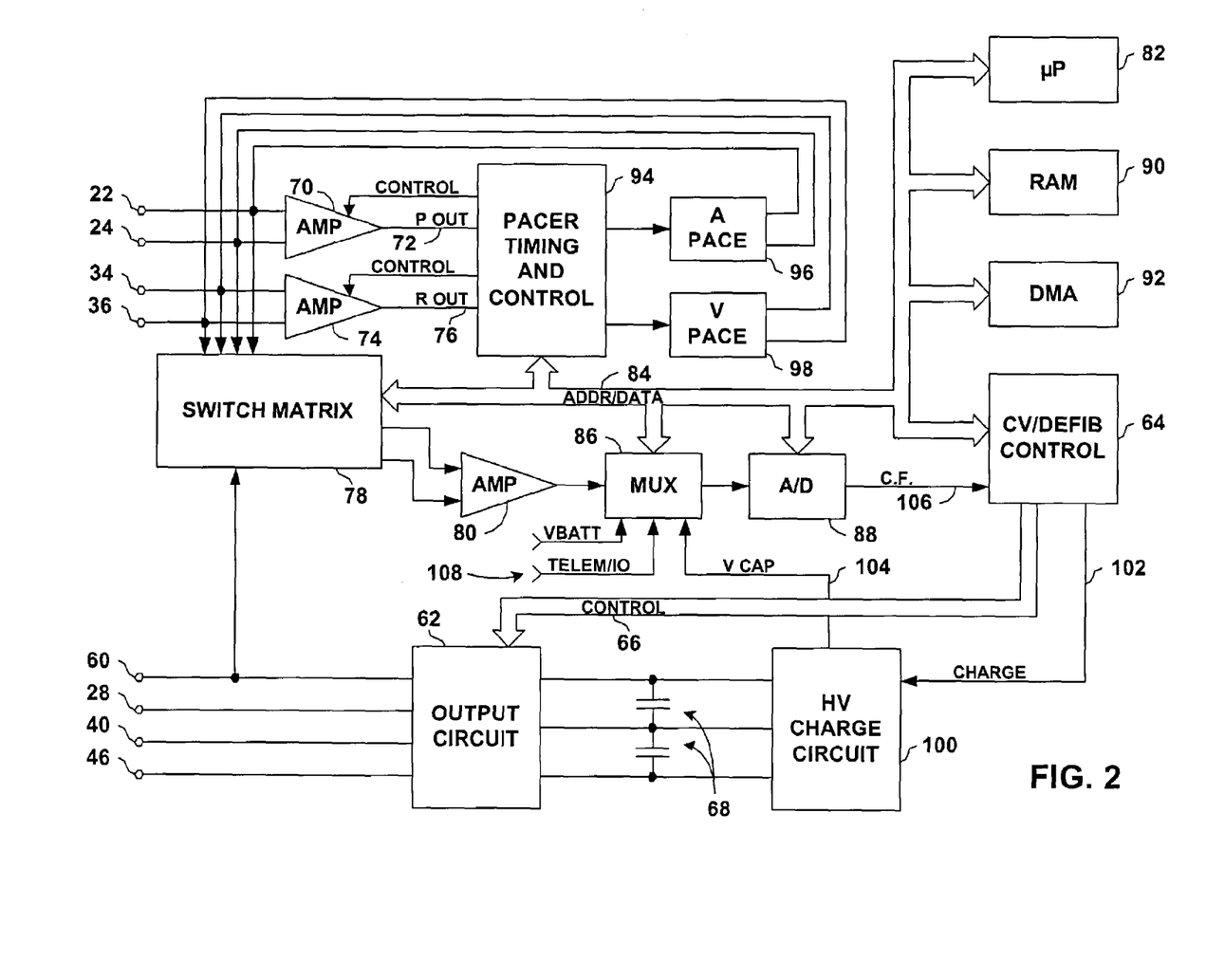
FIG. 2 is a block diagram of the implantable medical device depicted in FIG. 1.

FIG. 2 is a functional schematic diagram of one embodiment of IMD 10 and illustrates how IMD 10 delivers stimulations, performs capture tests and measures cardiac parameters. This diagram is exemplary of the type of device in which various embodiments of the invention may be embodied, and the invention is not limited to the particular schematic shown. On the contrary, the invention may be practiced in a wide variety of devices, including implantable devices that do not include cardioversion or defibrillation capability.

FIG. 2 includes electrode terminals 22, 24, 28, 34, 36, 40 and 46, which correspond to the electrodes shown in FIG. 1. Electrode 60 corresponds to the uninsulated portion of housing 52 of IMD 10. Electrodes 28, 40 and 46 are coupled to high voltage output circuit 62, which includes high voltage switches controlled by cardioversion/defibrillation (CV/defib) control logic 64 via control bus 66. Switches disposed within circuit 62 determine which electrodes are employed and which electrodes are coupled to the positive and negative terminals of a capacitor bank 68 during delivery of defibrillation pulses.

Electrodes 22 and 24, located on or in right atrium 14, are coupled to the P-wave amplifier 70. Amplifier 70 may comprise an automatic gain controlled amplifier providing an adjustable sensing threshold as a function of the measured P-wave amplitude. Amplifier 70 generates a signal on P-out line 72 whenever the signal sensed between electrodes 22 and 24 exceeds the sensing threshold. During capture testing, amplifier 70 determines whether right atrium 14 has been captured by determining whether the response of the atrium to a pacing stimulation exceed the sensing threshold.

Electrodes 34 and 36, located in right ventricle 16, are coupled to the R-wave amplifier 74. Amplifier 74 may comprise an automatic gain controlled amplifier providing an adjustable sensing threshold as a function of the measured R-wave amplitude. Amplifier 74 generates a signal on R-out line 76 whenever the signal sensed between electrodes 34 and 36 exceeds the sensing threshold of amplifier 74. Amplifier 74 may determine whether right ventricle 16 has been captured during capture testing.

A switch matrix 78 may select which of the available electrodes are coupled to wide band amplifier 80 for use in digital signal analysis. Selection of electrodes is controlled by microprocessor 82 via data/address bus 84. The signals from the selected electrodes are provided to multiplexer 86, and are thereafter converted to multi-bit digital signals by A/D converter 88. The signals may be stored in random access memory (RAM) 90 under control of direct memory access (DMA) circuit 92.

Microprocessor 82 may employ digital signal analysis techniques to characterize the digitized signals stored in RAM 90 to recognize and classify the patient's heart rhythm or to analyze the morphology of the signals employing any of several signal processing methodologies. During digital signal analysis, various cardiac parameters may be measured, such as the S-T segment, i.e., the duration between the conclusion of the depolarization marked by the QRS complex and the onset of repolarization marked by the T-wave.

Signals sensed via electrodes 22, 24, 34 and 36 may also be used for cardiac pacing, cardioversion and defibrillation therapies. Pacer timing/control circuitry 94 receives signals from P-out line 72 and R-out line 76, and computes various timing intervals as a function of the timing of the received signals. Pacer timing/control circuitry 94 also may include programmable digital counters that control pacing according to any of several pacing modes.

Pacer timing/control circuitry 94 may further regulate the strength and duration of pacing stimuli, under the control of microprocessor 82. Microprocessor 82 determines the desired strength and duration of pacing stimuli, and communicates these factors to pacer timing/control circuitry 94 via address/data bus 84. Pacer output circuitry 96 and 98, which are coupled to electrodes 22, 24, 34 and 36, generate the stimuli. The IPG of IMD 10 comprises microprocessor 82, in cooperation with pacer timing/control circuitry 94 and pacer output circuitry 96 and 98.

Pacer timing/control circuitry 94 may also compute intervals such as R-R intervals, P-P intervals, P-R intervals and R-P intervals. These intervals may be used to detect the presence of a tachyarrhythmia. Some forms of tachyarrhythmia may respond well to pacing.

When a cardioversion or defibrillation pulse is required, microprocessor 82 may control the timing, strength and duration of cardioversion and defibrillation pulses. In response to the detection of atrial or ventricular fibrillation or tachyarrhythmia requiring a cardioversion pulse, microprocessor 82 activates CV/defib control circuitry 64, which initiates charging of capacitor bank 68 via charging circuit 100, under the control of high voltage charging control line 102. The voltage on the high voltage capacitors is monitored via VCAP line 104, which is passed through multiplexer 86, and in response to reaching a predetermined value set by microprocessor 82, results in generation of a logic signal on Cap Full (CF) line 106 to terminate charging. A defibrillation or cardioversion pulse may be delivered by output circuit 62.

Microprocessor 82 may also receive, measure and analyze cardiac parameters detected by one or more sensors. Microprocessor 82 may, for example, measure the lead impedance of leads 18 and 20, by relating the quantity of current sent through a lead to the voltage potential needed to send that quantity of current. IMD 10 may also receive, measure and analyze other cardiac parameters sensed via electrodes 22, 24, 34 and 36, such as cardiac waveforms.

IMD 10 may receive, measure and analyze cardiac parameters detected via other sensors as well. For example, IMD 10 may receive blood pressure data directly from a pressure sensor (not shown) coupled to IMD 10 or indirectly from a pressure monitor (not shown). Microprocessor 82 may evaluate the blood pressure data and may identify pressures that may be of clinical significance. Sensors may respond to other conditions as well, such as the contractility of heart 12 or hemodynamic factors such as the pumping efficiency of heart 12.

IMD 10 may communicate with a person or another device via a telemetry or input/output module 108. The communication may employ any communication technique, such as radio, magnetic modulation, or ultrasound. In some embodiments of the invention, IMD 10 may communicate with the patient or a caregiver through a remote communication device such as a programmer or external monitor.

In other embodiments of the invention, IMD 10 may communicate with the patient by issuing an audible alarm that notifies the patient that there is or may be a problem with IMD 10, and that he should seek assistance. Some of the problems that may be detected by the techniques of the invention may warrant issuing an audible alarm, as the problems may be serious and may require prompt attention. For example, data collected by the techniques described below may show a trend indicating that the capture threshold is rising. Should the capture threshold rise too far, IMD 10 may lose all capability of capturing heart 12. Should IMD 10 lose all capability of capturing heart 12, then pacing therapies provided by IMD 10 may become ineffective, and the patient may suffer a decline in cardiac performance, or perhaps death.

A possibility of a loss of capture may be indicated by a cardiac capture test. A capture test is conventionally performed on a substantially periodic basis, typically once per day. The capture test may be performed at substantially the same time every day, but some embodiments of IMD 10 may change the time of the capture test. For example, IMD 10 may perform the capture test when the patient is resting, and may reschedule or postpone the capture test when cardiac parameters indicate that the patient is not resting.

A capture test is not the only indicator of a possibility of a loss of capture, however. Other cardiac parameters may be indicative of a potential for loss of capture as well. The invention includes techniques for using these other cardiac parameters to monitor changes to the capture threshold. These cardiac parameters may be measured more frequently than the capture test frequency, and may therefore provide an earlier indication of a potential problem than a capture test. When a change in one or more of these cardiac parameters indicates a possible change in the capture threshold, IMD 10 may increase the capture test frequency, and thereby monitor the capture threshold more closely.

Figure 3:
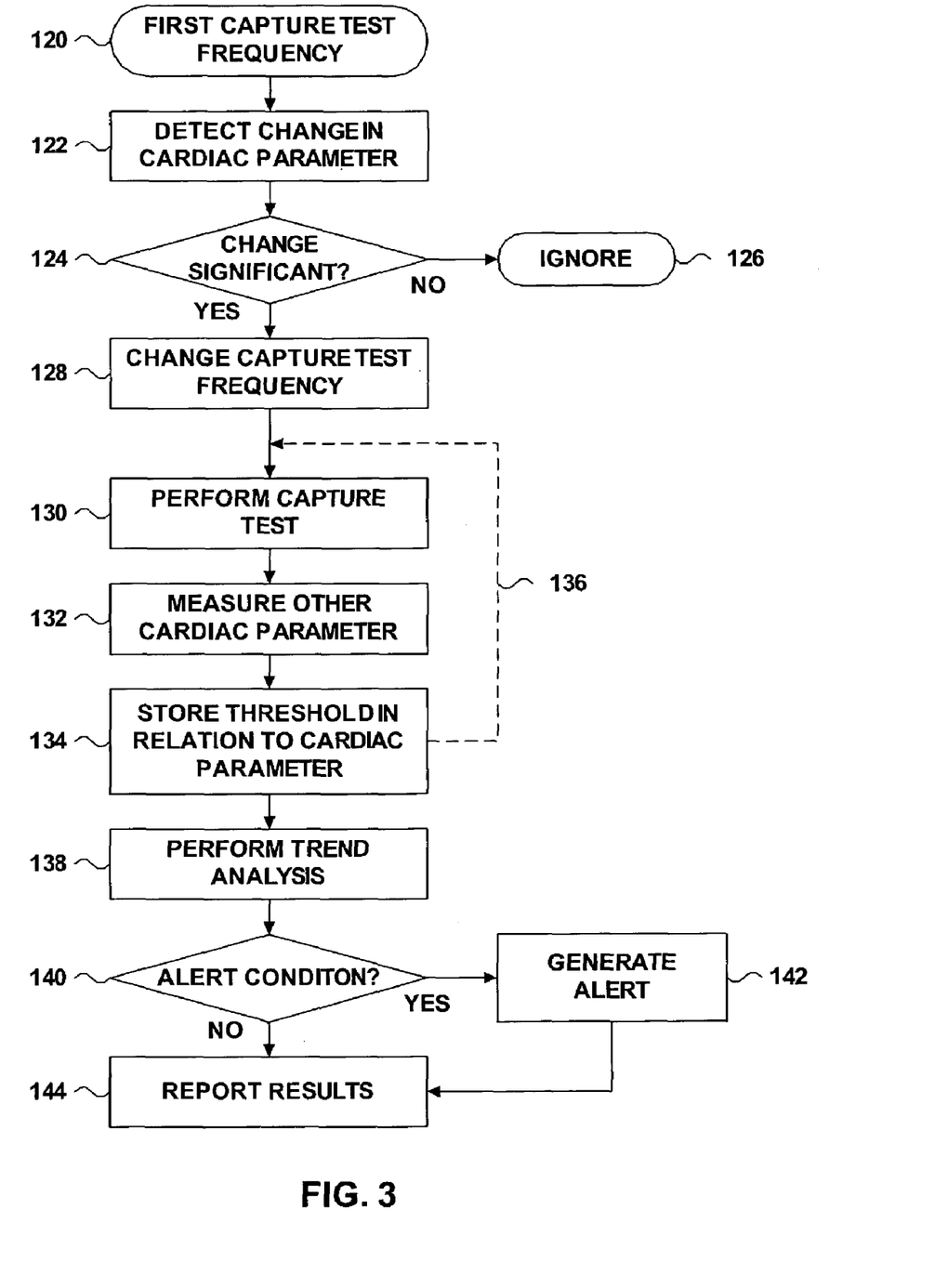
FIG. 3 is a flow diagram illustrating capture testing and measurement of another cardiac parameter.

FIG. 3 is a flow diagram illustrating use of cardiac parameters to monitor the capture threshold. At the outset, it is assumed that IMD 10 monitors the capture threshold by performing a cardiac capture test at a first capture test frequency (120), such as one time per day. As noted above, the first capture test frequency may be substantially periodic rather than strictly periodic, and IMD 10 may postpone or reschedule a capture test.

At some point, IMD 10 detects a change in a cardiac parameter (122). The cardiac parameter may be, for example, a change in lead impedance, or a change in a blood pressure of clinical significance, or a change in a cardiac waveform such as a change in the S-T segment, or a change in cardiac contractility detected by a contractility sensor. Not all such changes necessarily suggest that there is a change in the capture threshold, however. Accordingly, a processor in IMD 10 may determine whether the change in the cardiac parameter is significant (124), and if the change is not significant, the change is ignored (126).

When the change in the cardiac parameter is significant, however, IMD 10 changes the capture test frequency (128). In particular, IMD 10 increases the capture test frequency to a second frequency greater than the original frequency (120). Instead of performing a capture test one time per day, IMD 10 may perform a capture test (130) more often, such as once every fifteen minutes. A measurement of a cardiac parameter (132) may be made substantially contemporaneously with the capture test (130). The cardiac parameter need not be measured at,exactly the same time as the capture test, but the measurement should ordinarily take place at approximately the same time as the capture test, so that the measurement of the cardiac parameter may be substantially contemporaneous with the measurement of the capture threshold.

IMD 10 stores the capture threshold in relation to the measured cardiac parameter (134). The threshold may be stored as a function of the cardiac parameter, or vice versa. An example of a threshold in relation to a measured cardiac parameter will be given below in connection with FIG. 4. The cardiac parameter that is the subject of measurement (132) may be, but need not be, the same cardiac parameter for which an earlier change was detected (122).

The capture test (130), measurement of cardiac parameter (132) and the relation of the threshold to the cardiac parameter (134) may be repeated (136). By repetition of the above operations, it may be possible to gather enough data to perform a trend analysis (138). In some circumstances, the result of the trend analysis (138) may indicate that an alert condition is present (140), and in those circumstances, IMD 10 may generate an alert (142). The alert may be in the form of an audible alarm, for example, or in the form of an alert issued to an external monitor.

For example, repeated measurements of the capture threshold and lead impedance may indicate that the capture threshold is rapidly rising. The rapid rise may be due to fracture of a filament in a multifilar lead. The fracture may manifest itself with an increase in lead impedance and with an increase in the capture threshold.

A trend that shows an increase in lead impedance with an accompanying increase in the capture threshold may be used to diagnose a cause of an increase in the capture threshold, i.e., damage to a lead. The trend analysis may also be used to forecast a potential loss of capture. Because filament fractures in leads generally do not repair themselves and because lead damage is very likely to get worse, IMD 10 may generate an alert to notify the patient to seek prompt medical attention, or to notify another person that the patient may need prompt medical attention.

In other circumstances, however, an alert is not warranted (140). Not all changes in the capture threshold are dangerous. A change in capture threshold due to drug ingestion, for example, may result in a temporary increase in the capture threshold, and the capture threshold may return to normal after a time. When the capture threshold returns to normal, the capture test frequency may automatically revert to the original frequency (120). The results of the measurements may be included in a report that may be communicated to a person or an external device via telemetry or input/output module 108 (144).

Figure 4:
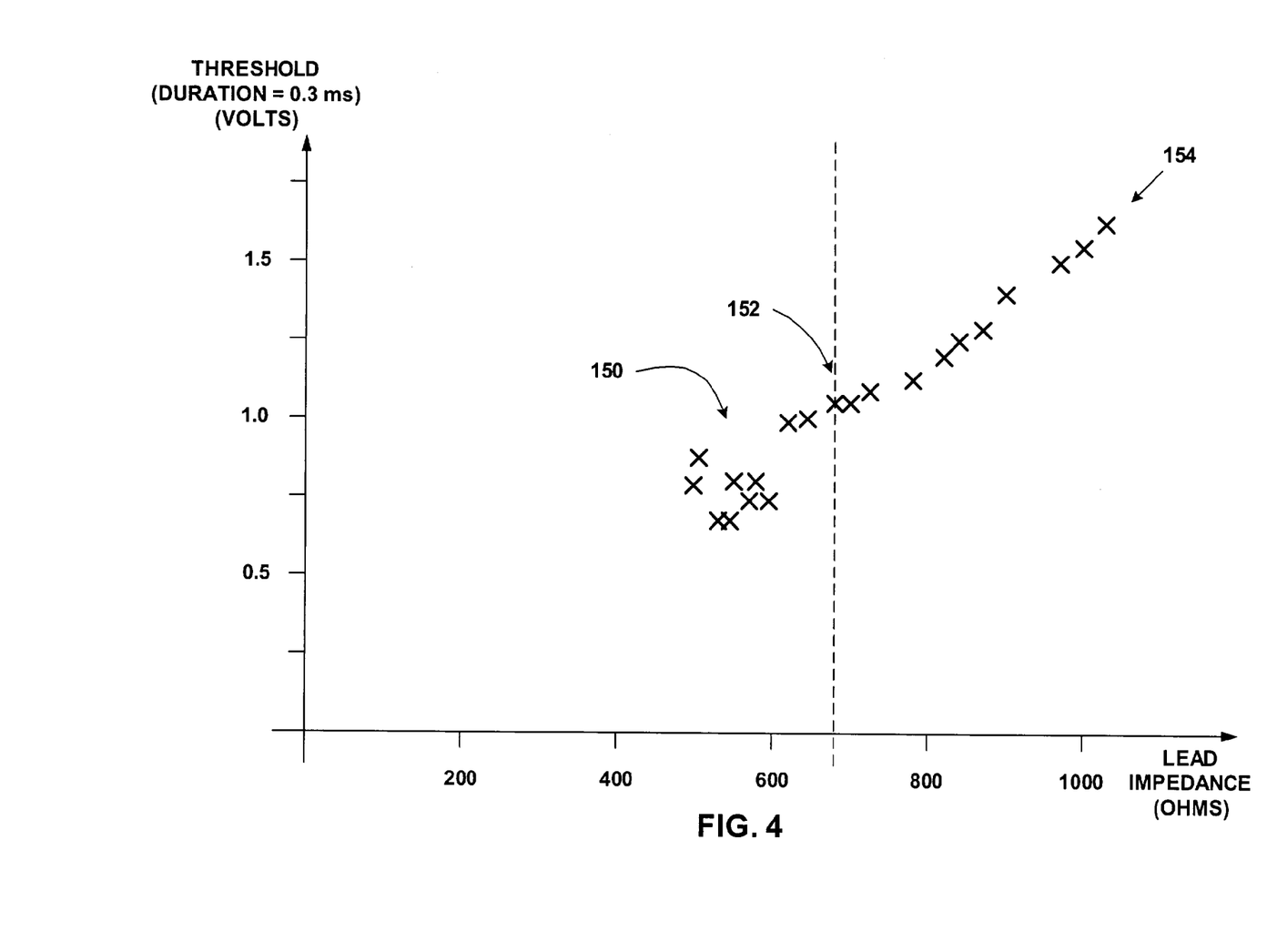
FIG. 4 is a graph illustrating application of the techniques of the invention.

FIG. 4 is a graph of exemplary data that illustrates application of the above techniques. In FIG. 4, the threshold strength in volts is plotted as a function of lead impedance in ohms. Threshold strength and lead impedance were measured substantially contemporaneously, with each measurement indicated by an "X." Threshold duration is assumed to be constant at 0.3 milliseconds.

Every measurement shows some difference in threshold strength and lead impedance. For a group of measurements 150, however, the changes from measurement to measurement are not significant. Measurements of lead impedance that fall below a preselected value 152 such as 680 ohms do not trigger a change in the capture test frequency.

When a measurement of lead impedance exceeds the preselected value 152, however, a change in the capture test frequency is triggered. The change in capture test frequency is triggered even if there is no significant change in the capture threshold itself. Instead of performing a capture test one time per day, IMD 10 may perform a capture test once every fifteen minutes, and may measure lead impedance at substantially the same time as IMD measures the capture threshold. IMD 10 stores the capture threshold measurements in relation to the lead impedance measurements. IMD 10 may also analyze the data to determine whether any trends are present.

In FIG. 4, data that are just barely above preselected value 152 demonstrate significant changes in lead impedance, with perhaps insignificant changes in the capture threshold. Subsequent data 154 above preselected value 152 demonstrate frequent significant changes in both lead impedance and threshold, and data 154 also demonstrate a direct relationship between lead impedance and threshold. Such a relationship may suggest that the changes in threshold are due to non-physiologic factors. In particular, the rapid rise in threshold may be caused by damage to a lead.

Analysis of data 154 may also be used to forecast changes in the capture threshold and to predict a need for medical attention. A steady rise in lead impedance and capture threshold, for example, may indicate that capture will be lost at a future time, when the IPG will be unable to generate a stimulus of sufficient strength or duration to capture the heart. In response to the trend indicated by data 154, IMD 10 may generate an alert to notify the patient to seek prompt medical attention before capture is lost.

The graph in FIG. 4 shows data plotted as a function of only two parameters. The measured data may, however, be plotted and analyzed for trends as a function of three or more parameters. Each data point may be plotted as a function of threshold, lead impedance and time, for example, which may be represented by a three-dimensional graph. The data may also be plotted in higher dimensions as well. For example, each data point may be plotted as a function of threshold strength, threshold duration, lead impedance and time, or as a function of threshold strength, threshold duration, lead impedance, blood pressure and time.

The invention may result in one or more advantages. Because conventional capture tests may involve considerable processor activity, and may therefore drain the power supply of an implantable device, the capture test frequency is typically infrequent. Conventional capture test frequencies may be one capture test per day or less frequent. Substantial changes to the capture threshold, however, may sometimes occur before the changes can be detected by a conventional capture test. The invention provides for capture tests to be performed on a more frequent basis when factors other than a detected change in the capture threshold indicate that the capture threshold should be monitored more closely.

An implantable medical device detects a change in significant lead impedance, for example, before detecting a significant change in capture threshold. And yet, the two parameters may be related. An increase in lead impedance may accompanied by or followed by a change in the capture threshold. By monitoring cardiac parameters other than the capture threshold, an implantable medical device may get an early warning of a potentially serious change in the capture threshold. Because of the early warning, the device may monitor the capture threshold more closely.

Once the capture threshold is being monitored, it may be advantageous to continue to monitor cardiac parameters other than the capture threshold. In addition, measuring a cardiac parameter substantially contemporaneously may be advantageous. A trend analysis may be useful in diagnosing the nature of the problem as well as forecasting a potential loss of capture. When a trend analysis indicates a serious problem or an impending loss of capture, the implantable medical device may generate an alert to notify the patient or another person that the patient needs prompt medical attention.

The preceding specific embodiments are illustrative of the practice of the invention. Various modifications may be made without departing from the scope of the claims. For example, the invention may be practiced by a variety of implantable medical devices that perform capture tests. Moreover, the cardiac parameters such as lead impedance or blood pressure are exemplary, and the invention is not limited to those parameters.

The invention may be embodied as a computer-readable medium that includes instructions for causing a programmable processor to carry out the methods described above. A "computer-readable medium" includes but is not limited to read-only memory, Flash memory and a magnetic or optical storage medium. The instructions may be implemented as one or more software modules, which may be executed by themselves or in combination with other software.

These and other embodiments are within the scope of the following claims.

The invention claimed is:

1. A method comprising:
   performing a first capture test to measure a capture threshold;
   measuring a first cardiac parameter substantially contemporaneously with the performance of the capture test;
   recording data representing the capture threshold in relation to the measurement of the cardiac parameter;

performing a second capture test to measure the capture threshold;

performing a second measurement of a cardiac parameter substantially contemporaneously with the performance of the second capture test;

recording data representing the capture threshold measured with the second capture test in relation to the second measurement of the cardiac parameter; and performing a trend analysis as a function of the recorded data.

2. The method of claim 1, further comprising forecasting a change to the capture threshold as a function of the trend analysis.

3. The method of claim 1, further comprising generating an alert as a function of the trend analysis.

4. The method of claim 1, wherein the cardiac parameter comprises at least one of a change in impedance of a lead used to deliver cardiac stimuli to a patient, a change in a blood pressure of the patient, a change in a cardiac waveform of the patient, a change in cardiac hemodynamics of the patient and a change in heart contractility of the patient.

5. A computer-readable medium comprising instructions for causing a programmable processor to:

perform a first capture test to measure a capture threshold;

measure a first cardiac parameter substantially contemporaneously with the performance of the capture test; and record data representing the capture threshold in relation to the measurement of the cardiac parameter;

perform a second capture test to measure the capture threshold;

perform a second measurement of a cardiac parameter substantially contemporaneously with the performance of the second capture test;

record data representing the capture threshold measured with the second capture test in relation to the second measurement of the cardiac parameter; and perform a trend analysis as a function of the recorded data.

6. The medium of claim 5, the instructions further causing the processor to forecast a change to the capture threshold as a function of the trend analysis.

7. The medium of claim 5, the instructions further causing the processor to generate an alert as a function of the trend analysis.

8. The medium of claim 5, wherein the cardiac parameter comprises at least one of a change in impedance of a lead used to deliver cardiac stimuli to a patient, a change in a blood pressure of the patient, a change in a cardiac waveform of the patient, a change in cardiac hemodynamics of the patient and a change in heart contractility of the patient.

* * * * *